(12) United States Patent
Bonev

(10) Patent No.: US 10,068,124 B2
(45) Date of Patent: Sep. 4, 2018

(54) SYSTEMS AND METHODS FOR SPOOF DETECTION BASED ON GRADIENT DISTRIBUTION

(71) Applicant: Synaptics Incorporated, San Jose, CA (US)

(72) Inventor: Boyan Bonev, San Jose, CA (US)

(73) Assignee: Synaptics Incorporated, San Jose, CA (US)

( * ) Notice: Subject to any disclaimer, the term of this patent is extended or adjusted under 35 U.S.C. 154(b) by 0 days.

(21) Appl. No.: 15/388,489

(22) Filed: Dec. 22, 2016

(65) Prior Publication Data
US 2018/0129857 A1 May 10, 2018

Related U.S. Application Data

(60) Provisional application No. 62/420,498, filed on Nov. 10, 2016.

(51) Int. Cl.
*G06K 9/00* (2006.01)
(52) U.S. Cl.
CPC ..... *G06K 9/00087* (2013.01); *G06K 9/00899* (2013.01)
(58) Field of Classification Search
None
See application file for complete search history.

(56) References Cited

U.S. PATENT DOCUMENTS

| 7,505,613 | B2 | 3/2009 | Russo |
| 9,390,311 | B2 * | 7/2016 | Kuo .................. G06K 9/00093 |
| 2010/0131273 | A1 | 5/2010 | Aley-Raz et al. |
| 2014/0294262 | A1 | 10/2014 | Schuckers et al. |

OTHER PUBLICATIONS

Kose, Neslihan, and Jean-Luc Dugelay. "Classification of captured and recaptured images to detect photograph spoofing." In Informatics, Electronics & Vision (ICIEV), 2012 International Conference on, pp. 1027-1032. IEEE, 2012.*
Assirati, Lucas, et al. "Performing edge detection by difference of gaussians using q-gaussian kernels." Journal of Physics: Conference Series. vol. 490. No. 1. IOP Publishing, 2014.*

(Continued)

*Primary Examiner* — Sumati Lefkowitz
*Assistant Examiner* — David Perlman
(74) *Attorney, Agent, or Firm* — Leydig, Voit & Mayer, Ltd.

(57) ABSTRACT

A system and method for performing spoof detection are disclosed. The method includes: receiving an input image of a biometric; generating a first filtered image by applying a first convolution to the input image based on a first convolution kernel; generating a second filtered image by applying a second convolution to the input image based on a second convolution kernel; computing a gradient residual image by subtracting, for each pixel location of the first and second filtered images, a pixel value in the second filtered image from a corresponding pixel value in the first filtered image; applying a density estimation procedure to the gradient residual image to identify areas of varied density; and, determining whether the input image is a replica of the biometric based on results of the density estimation procedure.

15 Claims, 6 Drawing Sheets

(56) References Cited

OTHER PUBLICATIONS

Mair, et al. "Adaptive and Generic Corner Detection Based on the Accelerated Segment Test," Proceeding ECCV'10, Proceedings of the 11th European Conference on Computer Vision: Part II, Heraklion, Crete, Greece, pp. 183-196 (Sep. 5-11, 2010).

Leutenegger, et al. "BRISK: Binary Robust Invariant Scalable Keypoints," 2011 IEEE International Conference on Computer Vision (ICCV) (Nov. 6-13, 2011).

Ojala, et al. "Multiresolution Gray Scale and Rotation Invariant Texture Classification with Local Binary Patterns," IEEE Transactions on Pattern Analysis and Machine Intelligence, vol. 24, Iss. 7, pp. 971-987 (Jul. 2002).

Dalal, et al. "Histograms of Oriented Gradients for Human Detection," IEEE Computer Society Conference on Computer Vision and Pattern Recognition 2005 (CVPR 2005) (Jun. 20-25, 2005).

Fisher, Bob. "Derivatives and Gradients" (Dec. 17, 1997) (available at: http://homepages.inf.ed.ac.uk/rbf/CVonline/LOCAL_COPIES/BASICMAT/node5.html).

Ghiani, et al. "Experimental Results on Fingerprint Liveness Detection," Proceeding AMDO '12, Proceedings of the 7th international conference on Articulated Motion and Deformable Objects, Mallorca, Spain, pp. 210-218 (Jul. 11-13, 2012).

Gottschlich, et al. "Fingerprint Liveness Detection based on Histograms of Invariant Gradients," 2014 IEEE International Joint Conference on Biometrics (IJCB) (Sep. 29-Oct. 2, 2014).

Wikipedia, "Image Gradient," as last modified on Sep. 15, 2016.

Pietikäinen, Matti. "Local Binary Patterns," Scholarpedia, vol. 5, No. 3 (2010).

Gragnaniello, et al. "An investigation of local descriptors for biometric spoofing detection," IEEE Transactions on Information Forensics and Security, vol. 10, Iss. 4, pp. 849-863 (2015).

Decann, et al. "A Novel Region Based Liveness Detection Approach for Fingerprint Scanners," Proceeding ICB '09, Proceedings of the Third International Conference on Advances in Biometrics, Alghero, Italy, pp. 627-636 (Jun. 2-5, 2009).

Ghiani, Luca, et al. "LivDet 2013 fingerprint liveness detection competition 2013." *2013 International Conference on Biometrics (ICB)*. IEEE, 2013.

Mura, Valerio, et al. "LivDet 2015 fingerprint liveness detection competition 2015." *Biometrics Theory, Applications and Systems (BTAS), 2015 IEEE 7th international Conference on*. IEEE, 2015.

* cited by examiner

SYSTEMS AND METHODS FOR SPOOF DETECTION BASED ON GRADIENT DISTRIBUTION

CROSS-REFERENCE TO RELATED APPLICATIONS

This application claims the benefit of U.S. Provisional Application No. 62/420,498, filed on Nov. 10, 2016, which is hereby incorporated by reference in its entirety.

FIELD

This disclosure generally relates to biometric sensors and, more particularly, to systems and methods for spoof detection based on gradient distribution.

BACKGROUND

Biometric authentication systems are used for authenticating and/or verifying users of devices incorporating the authentication systems. Biometric sensing technology provides a reliable, non-intrusive way to verify individual identity for recognition purposes.

Fingerprints, like various other biometric characteristics, are based on distinctive personal characteristics and, thus, are a reliable mechanism for recognizing an individual. There are many potential applications for utilization of fingerprint sensors. For example, fingerprint sensors may be used to provide access control in stationary applications, such as security checkpoints. Electronic fingerprint sensors may also be used to provide access control in mobile devices, such as cell phones, wearable smart devices (e.g., smart watches and activity trackers), tablet computers, personal data assistants (PDAs), navigation devices, and portable gaming devices. Accordingly, some applications, in particular applications related to mobile devices, may require authentication systems that are both small in size and highly reliable.

As used in the industry, biometric "spoofing" is any attempt to circumvent biometric security using a replica of a user's sensed biometric. In the context of fingerprint authentication systems, some examples of spoofing materials include three-dimensional (3D) gelatin molds of a finger, graphite and/or wood glue molds of a finger, and printed two-dimensional (2D) images of a finger, among others. In the context of facial recognition, an example spoofing material could be a photo of person's face. In the context of voice recognition, an example spoofing material could be a vocal imitation or playback.

As such, in order to maintain the integrity of biometric authentication systems, there is a need in the industry for anti-spoofing systems and methods, also referred to as "liveness detection" systems and methods, that can detect when an authentication attempt is a spoof and, upon spoof detection, properly deny authentication.

SUMMARY

Embodiments of the disclosure provide a method for spoof detection. The method includes: receiving an input image of a biometric; generating a first filtered image by applying a first convolution to the input image based on a first convolution kernel; generating a second filtered image by applying a second convolution to the input image based on a second convolution kernel; computing a gradient residual image by subtracting, for each pixel location of the first and second filtered images, a pixel value in the second filtered image from a corresponding pixel value in the first filtered image; applying a density estimation procedure to the gradient residual image to identify areas of varied density; and, determining whether the input image is a replica of the biometric based on results of the density estimation procedure. Some embodiments further include a non-transitory computer-readable storage medium storing instructions that, when executed by a processor, perform the method for spoof detection.

Another embodiment of the disclosure provides a device, comprising a biometric sensor and a processing system. The processing system is configured to: receive, from the biometric sensor, an input image of a biometric; generate a first filtered image by applying a first convolution to the input image based on a first convolution kernel; generate a second filtered image by applying a second convolution to the input image based on a second convolution kernel; compute a gradient residual image by subtracting, for each pixel location of the first and second filtered images, a pixel value in the second filtered image from a corresponding pixel value in the first filtered image; apply a density estimation procedure to the gradient residual image to identify areas of varied density; and, determine whether the input image is a replica of the biometric based on results of the density estimation procedure.

DETAILED DESCRIPTION

Figure 1:
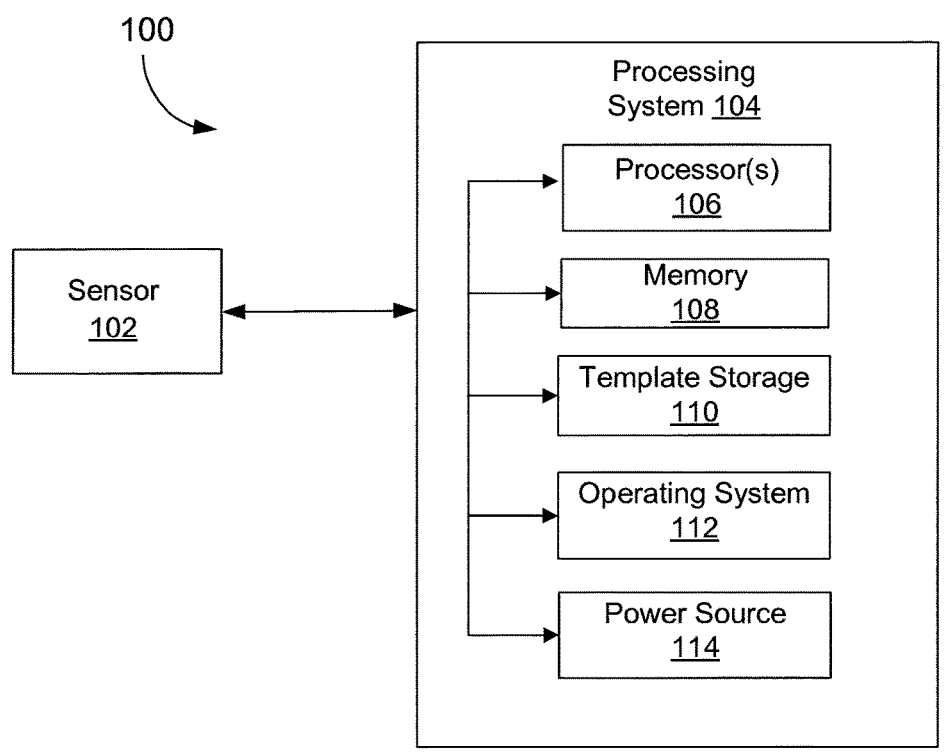
FIG. 1 is a block diagram of an example of a device that includes an optical sensor and a processing system according to an embodiment.

The following detailed description is merely exemplary in nature and is not intended to limit the disclosure or the application and uses of the disclosure. Furthermore, there is no intention to be bound by any expressed or implied theory presented in the preceding technical field, background, summary, brief description of the drawings, or the following detailed description. Turning to the drawings, and as described in greater detail herein, embodiments provide systems and methods for a gradient-based metric for spoof detection.

Fingerprint images can have considerable variation from person to person, from sensor to sensor, and even from different images for the same person. This variation reflects the fact that a person's finger is a living thing and changes as the finger responds to external factors, such as sweating, stretching when touched, etc. When a finger is imaged with a fingerprint sensor, these changes are captured to some extent and, hence, the sensed images include some variation, even with different impressions of the same finger. Also, different sensors from the same sensing technology can add minute differences.

The goal of a robust fingerprint matcher is to be agnostic to many of these changes for the same finger, which improves the usability of the system for a genuine user. However, if spoofs are constructed, e.g., with latent prints from the user, the spoof images can be sufficiently similar to the real finger that they can be used to gain entry into the system. Fingerprint anti-spoof technology attempts to distinguish images from spoof fingers from those of live fingers by deriving properties from the images that can be used to differentiate them.

As described, anti-spoof technology helps to improve the security of a biometric authentication system by preventing a successful authentication using a spoofed fingerprint, for example a spoof fingerprint created using the latent fingerprint of a genuine user of the device. Since the spoof fingerprint is a copy of the fingerprint that is enrolled on the device, without anti-spoof technology, a fingerprint matcher could match the spoofed fingerprint image to an enrolled image and grant access to the device.

Anti-spoof technology analyzes features in the spoof fingerprint image and attempts to distinguish the spoof fingerprint image from an image of a real finger. Embodiments of the disclosure provide a system and method for spoof detection based on gradient distribution.

As described in greater detail herein, some embodiments provide a spoof detection method based on the empirical observation that many spoof methods produce spoof images with irregular gradient distribution across the image. In some spoof methods, the reason why this gradient irregularity happens may be a result of spoof materials that do not have the same deformation properties as human skin, and/or the spoof creation process is not perfect, allowing some air, moisture, or particles to exist between the finger and the spoof material allowing uneven pressure over the spoof mold. Accordingly, some of the ridges and valleys in spoof images have smooth gradients and other ridges and valleys have stronger gradients in the same image of the spoof fingerprint. Visually, this appears as separate blurred regions and sharper regions in the same image. This effect is not observed in live fingerprint images, where the gradients are typically more evenly distributed across the image, and so all ridges and valley appear equally sharp.

Some embodiments provide a technique for spoof detection that involves applying convolutions to an input image using two different convolution kernels. For example, the applied convolution may be a Gaussian blur or other sub-Gaussian filter. In the context of a Gaussian blur, the Gaussian filter is applied to the input image using a first kernel (e.g., a first value for $\sigma$) and then the Gaussian filter is applied to the input image using a second kernel (e.g., a second value for $\sigma$). The resultant images are then subtracted from one another to generate a gradient residual image.

After the gradient residual image is obtained, the irregularity of the gradient residual image is quantified. Various techniques can be used to estimate the irregularity, including entropy estimation techniques, density estimation techniques, or dispersion estimation techniques, among others. The result obtained provides a metric that indicates whether there are any portions of the image that have "gaps" or irregularities in the density across the image.

Once the metric is computed, the metric can be input to a "classifier," which produces a score that can be compared against a threshold to determine if the finger is a live finger or a spoof. In some implementations, many different metrics are input into the classifier, and the classifier is configured to compute an overall liveness score based on the combination of metrics. In one example, the classifier is a neural network, but any classifier is within the scope of the disclosure. In one embodiment, the classifier itself can be developed using machine learning methods, where a training set and a test set are created to train and validate the classifier performance. In other embodiments, the classifier can be created without machine learning, but using any other kind of decision function.

Software-based anti-spoof technology detects spoofs by extracting features in an input image and analyzing those features to distinguish a spoof image from an image of a real finger. Typically, anti-spoof solutions are performed independent of the underlying matcher (i.e., the matcher that is used to determine whether the input image provides a match to an enrollment template for purposes of authentication, verification, or identification, for example), such that a match/non-match decision and a spoof/non-spoof decision are made separately and independently of one another.

Turning to the figures, FIG. 1 is a block diagram of an example of an electronic device 100 that includes a sensor device 102 (i.e., biometric sensor device) and a processing system 104, according to an embodiment. By way of example, basic functional components of the electronic device 100 utilized during capturing, storing, and validating a biometric match attempt are illustrated. The processing system 104 includes a processor(s) 106, a memory 108, a template storage 110, an operating system (OS) 112, and a power source(s) 114. Each of the processor(s) 106, the memory 108, the template storage 110, and the operating system 112 are interconnected physically, communicatively, and/or operatively for inter-component communications. The power source 114 is interconnected to the various system components to provide electrical power as necessary.

As illustrated, processor(s) 106 are configured to implement functionality and/or process instructions for execution within electronic device 100 and the processing system 104. For example, processor 106 executes instructions stored in memory 108 or instructions stored on template storage 110 to identify a biometric object or determine whether a biometric authentication attempt is successful or unsuccessful. Memory 108, which may be a non-transitory, computer-readable storage medium, is configured to store information within electronic device 100 during operation. In some embodiments, memory 108 includes a temporary memory, an area for information not to be maintained when the electronic device 100 is turned off. Examples of such temporary memory include volatile memories such as random access memories (RAM), dynamic random access memories (DRAM), and static random access memories (SRAM). Memory 108 also maintains program instructions for execution by the processor 106.

Template storage 110 comprises one or more non-transitory computer-readable storage media. In the context of a fingerprint sensor, the template storage 110 is generally configured to store information extracted from views for fingerprint images for a user's fingerprint or other enrollment/verification information. In some embodiments, verification views can also be stored in the template storage 110, for example, with template-update mechanisms. In some embodiments, the enrollment views may not be explicitly stored in the template storage 110, but rather some other information extracted from the enrollment views is stored that does not contain the original enrollment views themselves. In other embodiments, the enrollment views may be explicitly stored in the template storage 110. The enrollment views can include multiple images of the same finger. Further, the enrollment views can include view of multiple different fingers of the user. More generally, the template storage 110 may be used to store information about an object. The template storage 110 may further be configured for long-term storage of information. In some examples, the template storage 110 includes non-volatile storage elements. Non-limiting examples of non-volatile storage elements include magnetic hard discs, solid-state drives (SSD), optical discs, floppy discs, flash memories, or forms of electrically programmable memories (EPROM) or electrically erasable and programmable (EEPROM) memories, among others.

The processing system 104 also hosts an operating system (OS) 112. The operating system 112 controls operations of the components of the processing system 104. For example, the operating system 112 facilitates the interaction of the processor(s) 106, memory 108 and template storage 110. The processing system 104, although shown as including a processor 106 and memory 108, may further include a microprocessor, microcontroller and/or dedicated circuitry.

According to various embodiments, the processor(s) 106 implement hardware and/or software to obtain data describing an image of an input object. The processor(s) 106 may also align two images and compare the aligned images to one another to determine whether there is a match. The processor(s) 106 may also operate to reconstruct a larger image from a series of smaller partial images or sub-images, such as fingerprint images when multiple partial fingerprint images are collected during a biometric process, such as an enrollment or matching process for verification or identification.

The processing system 104 includes one or more power sources 114 to provide power to the electronic device 100. Non-limiting examples of power source 114 include single-use power sources, rechargeable power sources, and/or power sources developed from nickel-cadmium, lithium-ion, or other suitable material as well power cords and/or adapters which are in turn connected to electrical power.

Sensor device 102 can be implemented as a physical part of the electronic device 100, or can be physically separate from the electronic device 100. As appropriate, the sensor device 102 may communicate with parts of the electronic device 100 using any one or more of the following: buses, networks, and other wired or wireless interconnections. In some embodiments, sensor device 102 is implemented as a fingerprint sensor to capture a fingerprint image of a user. In accordance with the disclosure, the optical sensor device 102 uses optical sensing for the purpose of object imaging including imaging biometrics such as fingerprints. The sensor device 102 can be incorporated as part of a display, for example, or may be a discrete sensor. In some embodiments, the sensor device 102 may perform optical imaging. In various other embodiments, the sensor device 102 can be replaced with a capacitive sensor device, ultrasonic sensor device, or another sensor device that uses some other sensing technology for object imaging, as described in greater detail herein.

The electronic device 100 may utilize any suitable combination of sensor components and sensing technologies to detect user input in the sensing region. Some implementations utilize arrays or other regular or irregular patterns of multiple sensing elements to detect the input. Example sensing techniques that the electronic device 100 may use include capacitive sensing techniques, optical sensing techniques, acoustic (e.g., ultrasonic) sensing techniques, pressure-based (e.g., piezoelectric) sensing techniques, resistive sensing techniques, thermal sensing techniques, inductive sensing techniques, elastive sensing techniques, magnetic sensing techniques, and/or radar sensing techniques.

For example, the electronic device 100 may use resistive sensing techniques where contact from an input object closes an electrical circuit and can be used to detect input. In one example technique, the sensor device 102 includes a flexible and conductive first layer separated by one or more spacer elements from a conductive second layer. During operation, one or more voltage gradients are created across the layers. Pressing the flexible first layer may deflect it sufficiently to create electrical contact between the layers, resulting in voltage outputs reflective of the point(s) of contact between the layers. These voltage outputs may be used to determine spatial information corresponding to the input object.

In another example, the electronic device 100 may use inductive sensing techniques where one or more sensing elements pick up loop currents induced by a resonating coil or pair of coils. Some combination of the magnitude, phase, and frequency of the currents may then be used to determine spatial information corresponding to the input object.

In another example, the electronic device 100 may use acoustic sensing techniques where one or more acoustic sensing elements detect sound waves from nearby input objects. The sound waves may be in audible frequencies or ultrasonic frequencies. The detected sound waves may include echoes of ambient sound waves and/or echoes of sound waves emitted by the input device that are reflected from surfaces of the input object. Some combination of the amplitude, phase, frequency, and or time delay of the electrical signals may be used to determine spatial information corresponding to the input object.

One example acoustic sensing technique utilizes active ultrasonic sensing to emit high frequency source waves that propagate to the sensing region. One or more ultrasonic transmitter elements (also "ultrasonic emitters") may be used to emit high frequency sound waves to the sensing region, and one or more ultrasonic receiving elements (also "ultrasonic receivers") may detect echoes of the emitted sound waves. Separate elements may be used to transmit and receive, or common elements that both transmit and receive may be used (e.g., ultrasonic transceivers). In some instances, emitted ultrasonic waves are able to penetrate sub-surfaces of the input object, such as dermal layers of a human finger.

In another example, the electronic device 100 may use optical sensing techniques where one or more sensing elements detect light from the sensing region. The detected light may be reflected from the input object, transmitted through the input object, emitted by input object, or some combination thereof. The detected light may be in the visible or invisible spectrum (such as infrared or ultraviolet light). Example optical sensing elements include photodiodes, CMOS image sensor arrays, CCD arrays, thin-film detectors, and other suitable photosensors sensitive to light in wavelength(s) of interest. Active illumination may be used to provide light to the sensing region, and reflections from the sensing region in the illumination wavelength(s) may be detected to determine input information corresponding to the input object.

One example optical technique utilizes direct illumination of the input object, which may or may not be in contact with an input surface of the sensing region depending on the configuration. One or more light sources and/or light guiding structures are used to direct light to the sensing region. When an input object is present, this light is reflected directly from surfaces of the input object, which reflections can be detected by the optical sensing elements and used to determine input information about the input object.

Another example optical technique utilizes indirect illumination based on internal reflection to detect input objects in contact with an input surface of the sensing region. One or more light sources are used to direct light in a transmitting medium at an angle at which it is internally reflected at the input surface of the sensing region, due to different refractive indices at opposing sides of the interface defined by the input surface. Contact of the input surface by the input object causes the refractive index to change across this boundary, which alters the internal reflection characteristics at the input surface. Higher contrast signals can often be achieved if principles of frustrated total internal reflection (FTIR) are used to detect the input object, where the light is directed to the input surface at an angle of incidence at which it is totally internally reflected, except at locations where the input object is in contact and causes the light to scatter and partially transmit across this interface at the region of contact by the input object. An example of this is presence of a finger introduced to an input surface defined by a glass to air interface. The higher refractive index of human skin compared to air causes light incident at the input surface at the critical angle of the interface to air to be partially transmitted across the input interface and scattered by the finger, where it would otherwise be totally internally reflected at the glass to air interface. This optical response can be detected by the system and used to determine spatial information. In some embodiments, this can be used to image small scale surface variations of the input object, such as fingerprint patterns, where the internal reflectivity of the incident light differs depending on whether a ridge or valley of the finger is in contact with that portion of the input surface.

In another example, the electronic device 100 may use capacitive techniques where voltage or current is applied to create an electric field. Nearby input objects cause changes in the electric field, and produce detectable changes in capacitive coupling that may be detected as changes in voltage, current, or the like. Sensor electrodes may be utilized as capacitive sensing elements. Arrays or other regular or irregular patterns of capacitive sensing elements may be used to create electric fields. Separate sensor electrodes may be ohmically shorted together to form larger sensing elements.

One example technique utilizes "self capacitance" (or "absolute capacitance") sensing methods based on changes in the capacitive coupling between sensor electrodes and an input object. An input object near the sensor electrodes alters the electric field near the sensor electrodes, thus changing the measured capacitive coupling. An absolute capacitance sensing method may operate by modulating sensor electrodes with respect to a reference voltage (e.g. system ground), and by detecting the capacitive coupling between the sensor electrodes and the input object. For example, the sensing element array may be modulated, or a drive ring or other conductive element that is ohmically or capacitively coupled to the input object may be modulated. The reference voltage may by a substantially constant voltage or a varying voltage, or the reference voltage may be system ground.

Another example technique utilizes "mutual capacitance" (or "transcapacitance") sensing methods based on changes in the capacitive coupling between sensor electrodes. An input object near the sensor electrodes may alter the electric field between the sensor electrodes, thus changing the measured capacitive coupling. A transcapacitive sensing method may operate by detecting the capacitive coupling between one or more transmitter sensor electrodes (also "transmitter electrodes") and one or more receiver sensor electrodes (also "receiver electrodes"). Transmitter sensor electrodes may be modulated relative to a reference voltage to transmit transmitter signals. Receiver sensor electrodes may be held substantially constant relative to the reference voltage to facilitate receipt of resulting signals. The reference voltage may by a substantially constant voltage or system ground. The transmitter electrodes are modulated relative to the receiver electrodes to transmit transmitter signals and to facilitate receipt of resulting signals. A resulting signal may comprise effect(s) corresponding to one or more transmitter signals, and/or to one or more sources of environmental interference (e.g. other electromagnetic signals). Sensor electrodes may be dedicated transmitters or receivers, or may be configured to both transmit and receive. Also, sensor electrodes may be dedicated transcapacitance sensing elements or absolute capacitance sensing elements, or may be operated as both transcapacitance and absolute capacitance sensing elements.

Some non-limiting examples of electronic devices 100 include personal computers of all sizes and shapes, such as desktop computers, laptop computers, netbook computers, tablets, web browsers, e-book readers, and personal digital assistants (PDAs). Additional example electronic devices 100 include composite input devices, such as physical keyboards and separate joysticks or key switches. Further example electronic devices 100 include peripherals such as data input devices (including remote controls and mice) and data output devices (including display screens and printers). Other examples include remote terminals, kiosks, video game machines (e.g., video game consoles, portable gaming devices, and the like), communication devices (including cellular phones, such as smart phones), and media devices (including recorders, editors, and players such as televisions, set-top boxes, music players, digital photo frames, and digital cameras). Still further examples include vehicles, firearms, and other devices that may require to be locked or need authentication.

Figure 2:
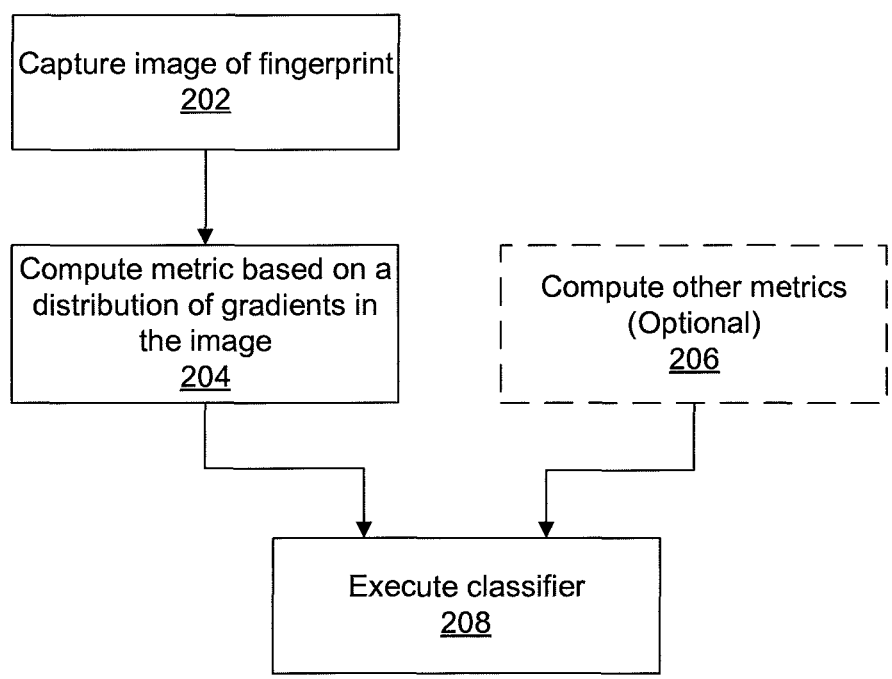
FIG. 2 is a block diagram illustrating a system and method for spoof detection involving a metric based on a distribution of gradients in the image according to an embodiment.

FIG. 2 is a block diagram illustrating a system and method for spoof detection involving a metric based on a distribution of gradients in the image according to an embodiment. At step 202, a sensor captures an image of a fingerprint. The fingerprint can be either from a live finger or a spoofed finger. At step 204, a processor computes a metric based on a distribution of gradients in the image, as described in greater detail herein. The metric computed at step 204 is passed to a classifier. Optionally, at step 206, the processor may compute other spoof detection metrics and also pass them to the classifier. At step 208, the processor executes the classifier to determine whether the image of the fingerprint captured at step 202 is from a live finger or a spoofed finger. In some embodiments, the spoof detection classifier is executed as part of a fingerprint matcher that compares an input image to enrollment images. In other embodiments, the spoof detection classifier is executed separately from the fingerprint matcher.

Figure 3:
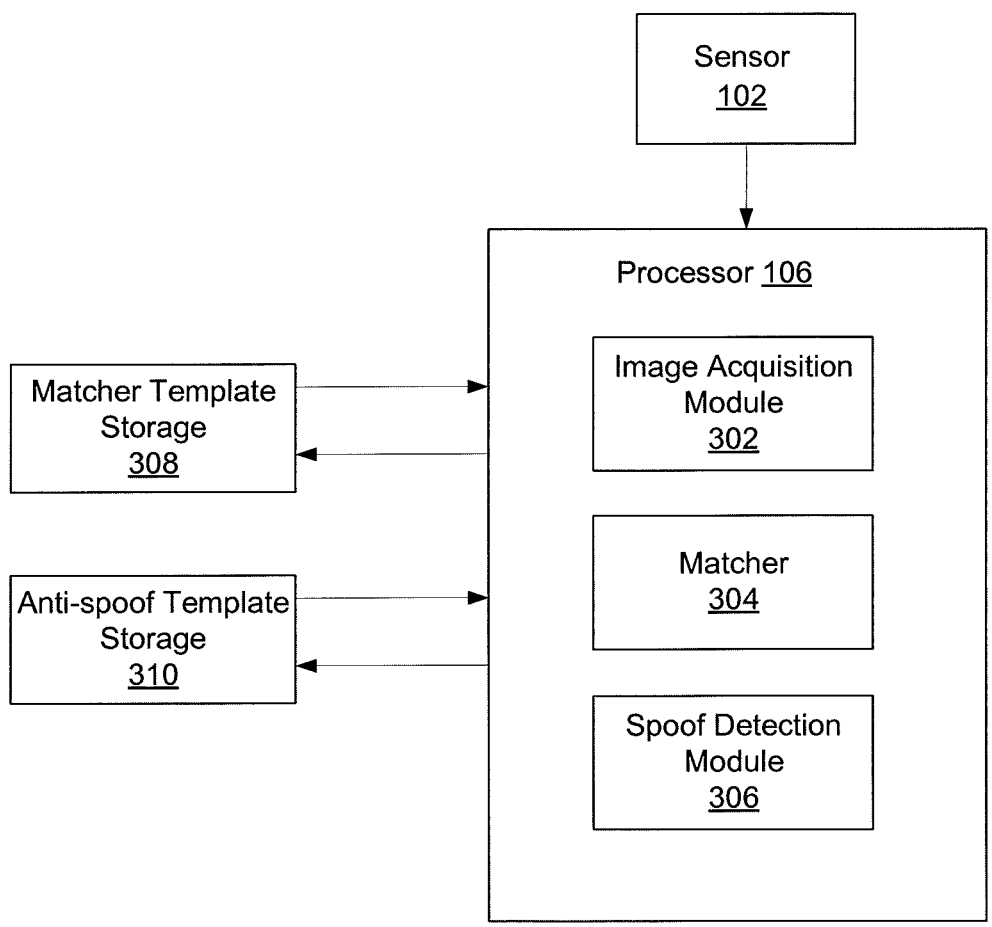
FIG. 3 is a block diagram of a spoof detection system, according to an embodiment.

FIG. 3 is a block diagram of a spoof detection system, according to an embodiment. The system includes a sensor device 102 and a processor 106. The processor 106 is configured to execute one or more software functional blocks, including an image acquisition module 302, a matcher 304, and a spoof detection module 306. The image acquisition module 302, the matcher 304, and the spoof detection module 306 are implemented as software instructions stored in a memory and executed by one or more processors 106. It is understood that each of the functional blocks may be also implemented by dedicated circuitry instead of or in combination with software.

Although shown as separate function blocks in FIG. 3, two or more of the image acquisition module 302, the matcher 304, and the spoof detection module 306 may be executed together as a single software module, application, or operating system. Alternatively, the image acquisition module 302, the matcher 304, and the spoof detection module 306 may be executed separately and/or provided by different software vendors. Also, in some embodiments, multiple processors 106 may be used to execute one or more of the image acquisition module 302, the matcher 304, and the spoof detection module 306.

In some embodiments, an input image, such as a fingerprint image, is captured by the sensor device 102. The input image is passed to the image acquisition module 302, which determines whether the image is an enrollment image or a verification image. If the input image is an enrollment image, a template associated with the input image is stored in a matcher template storage 308 and/or the matcher template storage 308 is updated based on the new input image.

If the input image is a verification image, the image acquisition module 302 also passes the input image to the matcher 304, which is configured to determine whether the input image matches any of the enrollment images stored in the matcher template storage 308. In one implementation, the matcher 304 may compare the input image to the enrollment image to determine a difference between the images. In some embodiments, if the difference is below a threshold, a match is found; otherwise, there is no match. In other embodiments, various techniques other than a comparison to a threshold can be used to determine whether the input image is a match to any of the enrollment images. Many different techniques can be used to execute the matcher 304, including point-based techniques, ridge-based techniques, or a combination of point-based and ridge-based techniques.

In one implementation, before the matcher 304 can compare the input image to the stored enrollment images (or "templates"), the matcher 304 performs alignment. An alignment that most closely aligns the input image to one of the enrollment images is determined, and transformation corresponding to the alignment is applied to the input image. The transformation T can be represented by $T=(T_x, T_y, \theta)$, where $T_x$ is a translation in the horizontal direction, $T_y$ is a translation in the vertical direction, and $\theta$ is a rotation. This process is known as image alignment. Various techniques may be used by the matcher 304 to compute the image alignment.

In one embodiment, after the matcher 304 performs image alignment, the matcher 304 makes a match/non-match decision. In other embodiments, the matcher generates a match score and returns the match score to another entity of the system that called the matcher 304 (e.g., the image acquisition module 302), where the other entity makes the match/non-match decision based on the match score. The match/non-match decision may be based on comparing overlapping regions of the input image and the enrollment image. In one implementation, the matcher 304 may compare the overlapping regions of the aligned input image to the enrollment image to determine a difference between the images. In some embodiments, if the difference is below a threshold, a match is found; otherwise, there is no match. It should be understood that many different techniques can be used for matching and are also within the scope of the disclosure.

In some embodiments, for enrollment images, the image acquisition module 302 also passes the input image to the spoof detection module 306, which may extract anti-spoof metrics from the input image. Example anti-spoof metrics include: an average gray level of ridges, an average gray level of valleys, one or more values as to whether the input image includes blurred areas, one or more values as to whether the input image includes relative lighter areas, one or more values as to whether the input image includes relative darker areas, texture information (for example, by computing LBP (linear binary patterns) on portions of the input image, among others. In some implementations, the anti-spoof metrics may not be discerning enough to provide adequate fingerprint matching results, i.e., since many spoofed images could satisfy a matcher that relied solely on anti-spoof metrics for matching.

The anti-spoof metrics extracted from the input image by the spoof detection module 306 are stored in an anti-spoof template (which can also be referred to as an "anti-spoof enrollment template") in the anti-spoof template storage 310. In some embodiments, the metrics extracted from the input image can be combined with the anti-spoof metrics in the anti-spoof template, for example by averaging the metrics extracted from the input image and the anti-spoof metrics in the anti-spoof template, to generate an updated anti-spoof template. Some embodiments do not store an anti-spoof template, and the spoof/non-spoof decision is based solely on the input image.

In one implementation, the matcher template storage 308 and the anti-spoof template storage 310 comprise one storage device. In another implementation, the matcher template storage 308 and the anti-spoof template storage 310 comprise separate storage devices.

In addition, in one implementation, when a user is enrolling enrollment images, the same images are used for updating the matcher template storage 308 and the anti-spoof template storage 310. In other implementations, separate enrollment processes are used to update the matcher template storage 308 and the anti-spoof template storage 310. As such, a given enrollment image could be used to update just one or both of the matcher template storage 308 and the anti-spoof template storage 310. However, as described, other embodiments do not store any anti-spoof templates, and the spoof/non-spoof decision is based solely on the input image.

In some embodiments, if the matcher 304 does not find a match in the matcher template storage 308, then the matcher 304 takes an appropriate action, such as, for example, denying entry to a mobile device. If the matcher 304 finds a match, then the spoof detection module 306 is configured to determine whether the input image is a spoof of a live finger, i.e., whether image is that of a real live finger or a other non-derma-based material, such as gelatin or wood glue.

In some embodiments, the spoof detection module 306 is executed as part of the matcher 304. In other embodiments, the spoof detection module 306 is executed separately from the matcher 304.

In some embodiments, the spoof detection module 306 is executed after the matcher 304 finds a positive match. In other embodiments, the spoof detection module 306 is executed before the matcher 304 makes a match/non-match decision. In still further embodiments, the spoof detection module 306 and the matcher 304 are executed in parallel.

Also, in some embodiments, the match/non-match decision of the matcher is made by a classifier associated with the matcher, which is the same classifier that makes the spoof/non-spoof decision. In other embodiments, the match/non-match decision is made by a different classifier than the classifier that makes the spoof/non-spoof decision.

Figure 4:
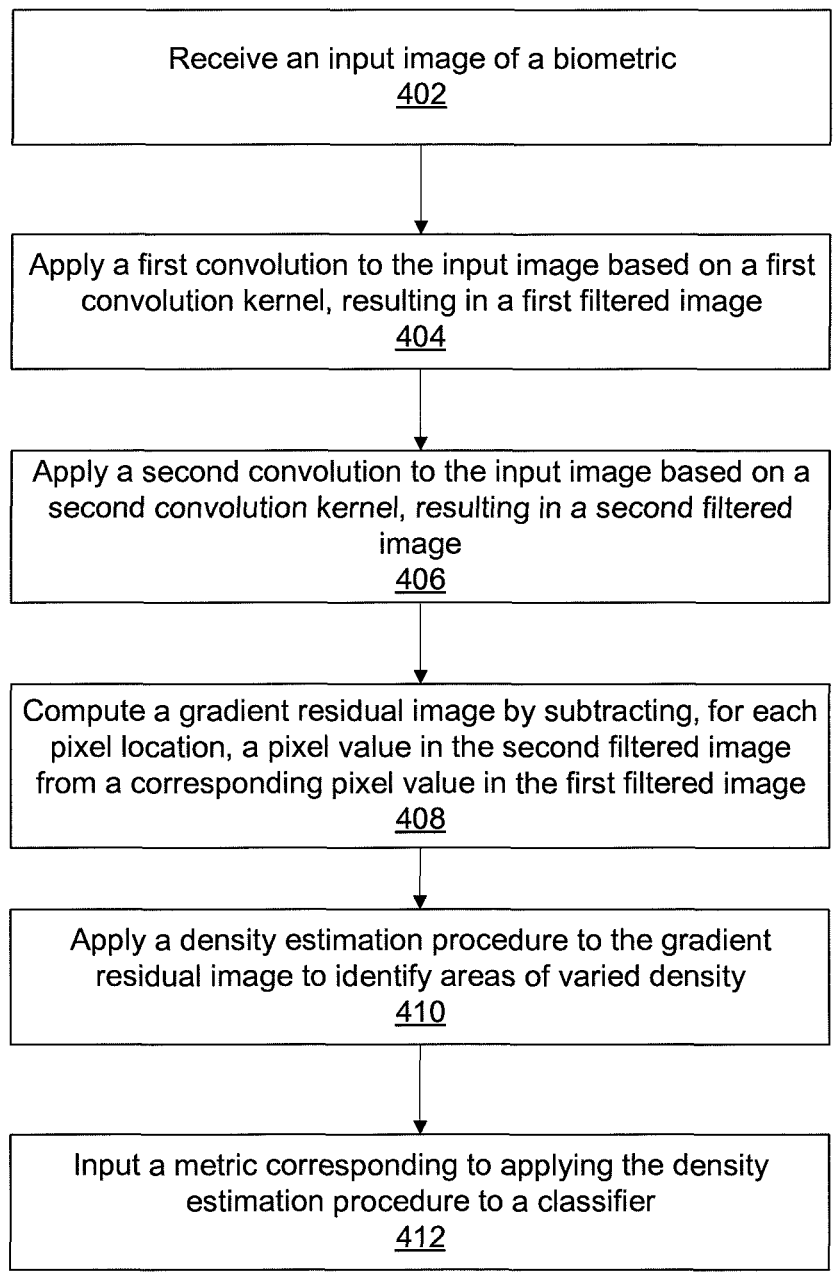
FIG. 4 is a flow diagram illustrating method steps for computing a metric based on a distribution of gradients in an image according to an embodiment.

FIG. 4 is a flow diagram illustrating method steps for computing a metric based on a distribution of gradients in an image according to an embodiment. In one embodiment, the method illustrated in FIG. 4 corresponds to step 204 in FIG. 2.

As shown in FIG. 4, at step 402, a processor receives an input image of a biometric. In one embodiment, the input image is the image captured at step 202 in FIG. 2. In another embodiment, the input image is a down-sampled or sub-sampled version the image captured at step 202 in FIG. 2. In some implementations, the input image is a grayscale image of a fingerprint.

At step 404, the processor applies a first convolution to the input image based on a first convolution kernel, resulting in a first filtered image. In one implementation, the first convolution is a Gaussian filter. In other embodiments, the first convolution is a sub-Gaussian filter or any other type of smoothing function. In one implementation, the Gaussian filter may be implanted using the equation:

$$G(x, y) = \frac{1}{2\pi\sigma^2} e^{-\frac{x^2+y^2}{2\sigma^2}},$$

where x is the distance from the origin in the horizontal axis, y is the distance from the origin in the vertical axis, and σ is the standard deviation of the Gaussian distribution. In the context of Gaussian filtering, the first convolution kernel comprises the value for σ. For example, the first convolution kernel may be σ=1.1.

At step 406, the processor applies a second convolution to the input image based on a second convolution kernel, resulting in a second filtered image. Similar to the first convolution, the second convolution may be a Gaussian filter, a sub-Gaussian filter, or any other type of smoothing function. Continuing with the example of Gaussian filtering, the second convolution kernel may be σ=1.4.

In addition, the first and second convolutions can be applied to the input image in a plurality of different ways. In a first implementation, the first and second convolutions have the same parameters for all images. In the context of Gaussian filtering, the values for σ can be constant across all images to which the method is applied. The settings for the first and second convolutions can be learned from a dataset of a subset of images that is representative.

In a second implementation, the first and second convolutions have different parameters based on individual or particular fingers, given a set of enrollment images. In some cases, a person's finger may have blurry areas (e.g., due to scarring, cuts, or simply the nature of the fingerprint). The method may take such information into account when setting the parameters of the first and second convolutions.

In a third implementation, if the image has already been matched by a matcher to one or more enrollment images, the gradients distribution could be compared to the one that is to be expected in only the overlapping regions.

Referring back to FIG. 4, at step 408, the processor computes a gradient residual image by subtracting, for each pixel location, a pixel value in the second filtered image from a corresponding pixel value in the first filtered image.

When subtracting these two images, the resulting gradient residual outlines the ridges if the gradient are strong enough not to be blurred out. In the parts of the image where the gradients are weaker, the gradient residual will likewise be very weak.

Figure 5B:
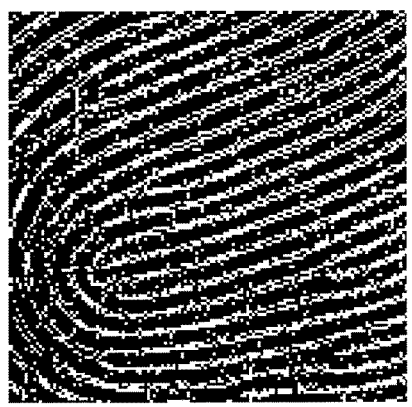
FIG. 5B is an example of a gradient residual image of the live fingerprint in FIG. 5A according to an embodiment.
Figure 5A:
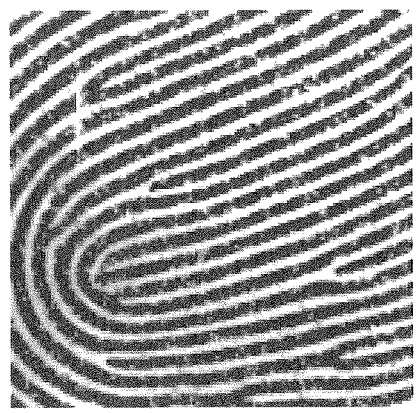
FIG. 5A is an example of a grayscale image of a live fingerprint according to an embodiment.
Figure 6A:
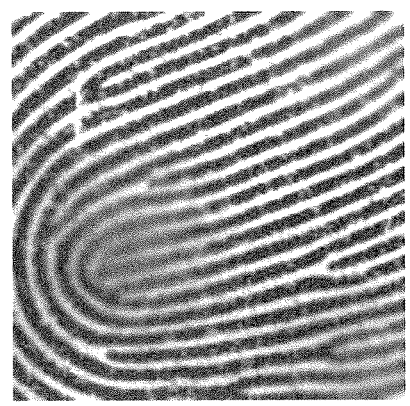
FIG. 6A is an example of a grayscale image of a spoofed fingerprint according to an embodiment.

FIGS. 5A-6B illustrate examples of this implementation. FIG. 5A is an example of a grayscale image of a live fingerprint according to an embodiment. FIG. 5B is an example of a gradient residual image of the live fingerprint in FIG. 5A according to an embodiment. The gradient residual image in FIG. 5B is binarized to show only pixels where the residual is stronger than 20% of the maximum residual in the image.

Figure 6B:
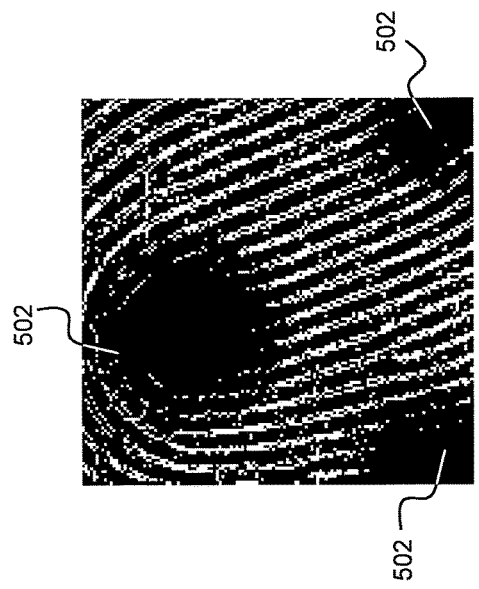
FIG. 6B is an example of a gradient residual image of the spoofed fingerprint in FIG. 6A according to an embodiment.

As can be seen by comparing the images in FIG. 5B (i.e., gradient residual of live fingerprint) and FIG. 6B (i.e., gradient residual of spoofed fingerprint), there are areas 502 of the image in FIG. 6B that have irregular gradient distribution, which is an indicator that the fingerprint from which the image is generated is a spoofed fingerprint. By contrast, in the image in FIG. 5B, the density is similar across the whole image.

According to the disclosed embodiments, the irregular gradient distribution is quantified to be a useful metric in liveness detection. Referring again to FIG. 4, at step 410, the processor applies a density estimation procedure to the gradient residual image to identify areas of varied density. According to various embodiments, and as described in greater detail below in FIG. 7, various techniques can be used to estimate the irregularity, including entropy estimation techniques, density estimation techniques, or dispersion estimation techniques, among others.

At step 412, the processor inputs a metric corresponding to applying the density estimation procedure to a classifier configured to determine whether an image is a spoof. As described, other metrics can also be input into the classifier. For example, other metrics may include both local image descriptors (such as metrics from scale-invariant feature transform) and global image descriptors (such as histograms of intensities, gradients, etc.). In one embodiment, the classifier is configured to make a spoof/non-spoof decision based on an overall liveness score that is computed by the classifier based on the combination of metrics. In another embodiment, the classifier is configured to generate the overall liveness score and return the overall liveness score to another entity within the anti-spoof module that makes the spoof/non-spoof decision, e.g., by comparing the anti-spoof score to a threshold. In one example, the classifier is a neural network, but any classifier is within the scope of the disclosure. The classifier itself can be developed using machine learning methods, where a training set and a test set are created to train and validate the classifier performance.

Figure 7:
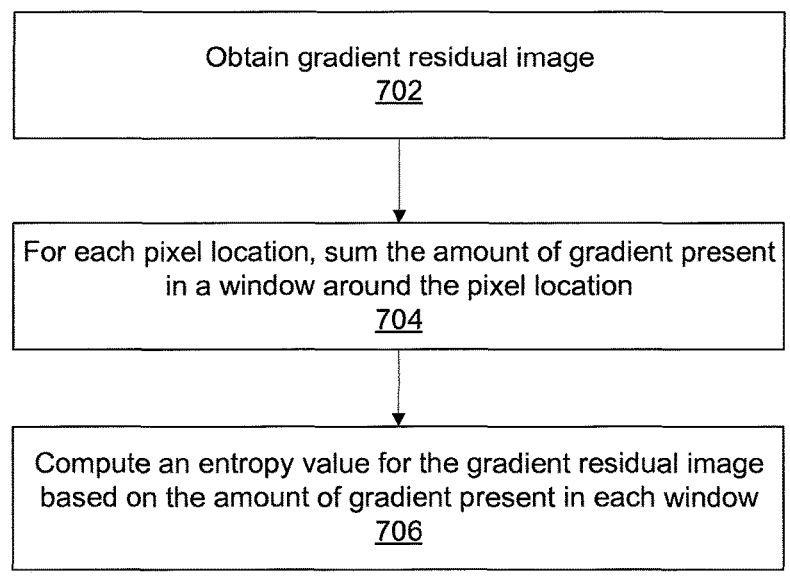
FIG. 7 is a flow diagram illustrating method steps for computing measure of uniformity of the density of an image according to an embodiment.

FIG. 7 is a flow diagram illustrating method steps for computing measure of uniformity of the density of an image according to an embodiment.

At step 702, a processor obtains gradient residual image. For example, the gradient residual image may be obtained by performing steps 402-404-406-408 in FIG. 4.

At step 704, the processor, for each pixel location in the gradient image, sums the amount of gradient present in a window around the pixel location. In one implementation, each pixel in the gradient image is examined. In an alternate implementation, each n pixels in the gradient image are examined, where n>1. The window around each pixel (or n pixels) may be square-shaped window of fixed size. Alternatively, the window size may vary with image size or other factors. According to various embodiments, the windows overlap one another.

At step 706, the processor, computes an entropy value for the gradient residual image based on the amount of gradient present in each window. The entropy value is a measure of how uniform the density is across the whole image.

In one implementation, computing the entropy value comprises first calculating an average density value of the windows in the gradient image, and then determining how many windows have a density value that deviates by a first threshold ($T_1$) from the average density value. The count of such windows may be compared to a second threshold ($T_2$) to determine whether the image is a spoof. For example, if the count of such windows is greater than $T_2$, then the image is determined to be a spoof.

In another implementation, computing the entropy value comprises identifying the single window with the lowest density. The density value of such a window can be compared to a threshold ($T_3$) to determine whether the image is a spoof. For example, if the density of such window is less than $T_3$, then the image is determined to be a spoof.

In some embodiments, the various thresholds (i.e., $T_1$, $T_2$, $T_3$) an be varied based on the enrollment images of the finger. In some cases, a person's finger may have blurry areas (e.g., due to scarring, cuts, or simply the nature of the fingerprint). The method may take such information into account when setting the values of the various thresholds.

In other embodiments, rather than using overlapping windows to compute an entropy value, the entropy value can be computed by implementing a nearest-neighbor technique. In one implementation of a nearest-neighbor technique, in the residual image, the average distance from each pixel to its nearest non-empty pixel (this is another formulation of the distance transform) is correlated with a density estimation.

The entropy value (or other metric) computed at step 706 can be input to a classifier that performs the spoof detection. Examples of metrics that can be passed to the classifier include: an average window density of the gradient residual image, a count of windows that deviate by a certain threshold from the average density, and/or a density value of the window having the lowest density. As described, the classifier is configured to compute an overall liveness score based on a combination of metrics.

Advantageously, embodiments of the disclosure provide a metric for spoof detection that yields a good separability of spoofed fingers versus live fingers. This metric can be used on single images (i.e., without any reference images of the finger) or in the presence of enrollment views (i.e., using the enrollment views as references for obtaining a more specific prior image density). The metric can be used on its own or in combination with other metrics to boost spoof detection performance. The metric can be used to detect spoofs made out of different spoofing materials.

Although this invention describes optical object imaging in the context of fingerprint image sensing, the method and system may be used to image any object.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for spoof detection, comprising:
  receiving an input image of a biometric;
  generating a first filtered image by applying a first convolution to the input image based on a first convolution kernel;
  generating a second filtered image by applying a second convolution to the input image based on a second convolution kernel;
  computing a gradient residual image by subtracting, for each pixel location of the first and second filtered images, a pixel value in the second filtered image from a corresponding pixel value in the first filtered image;
  applying a density estimation procedure to the gradient residual image to identify areas of varied density; and
  determining whether the input image is a replica of the biometric based on results of the density estimation procedure,
  wherein applying the density estimation procedure comprises:
    for each pixel location of the gradient residual image, summing an amount of gradient present in a window around the pixel location to generate a density value of the window around the pixel location;
    computing an average density value of the density values of the windows;
    determining a count of a number of windows that have a density value that deviates from the average density value by a threshold amount; and
    identifying areas of varied density based on the count.

2. The method of claim 1, wherein the window around each pixel location is a square-shaped window that overlaps at least one other window corresponding to a different pixel location.

3. The method of claim 1, wherein the first convolution comprises a Gaussian blur, and the first convolution kernel comprises a standard deviation of a Gaussian distribution.

4. The method of claim 1, wherein determining whether the input image is a replica of the biometric is further based on applying a density estimation procedure to one or more enrollment images of the biometric.

5. The method of claim 1, wherein the biometric comprises a fingerprint of a finger, and the replica comprises a gelatin mold, a graphite mold, or a wood glue mold of the fingerprint of the finger.

6. A non-transitory computer-readable storage medium storing instructions that, when executed by a processor, causes a computing device to perform spoof detection, by performing steps comprising:
   receiving an input image of a biometric;
   generating a first filtered image by applying a first convolution to the input image based on a first convolution kernel;
   generating a second filtered image by applying a second convolution to the input image based on a second convolution kernel;
   computing a gradient residual image by subtracting, for each pixel location of the first and second filtered images, a pixel value in the second filtered image from a corresponding pixel value in the first filtered image;
   applying a density estimation procedure to the gradient residual image to identify areas of varied density; and
   determining whether the input image is a replica of the biometric based on results of the density estimation procedure,
   wherein applying the density estimation procedure comprises:
      for each pixel location of the gradient residual image, summing an amount of gradient present in a window around the pixel location to generate a density value of the window around the pixel location;
      determining a window having a smallest density value; and
      identifying areas of varied density based on the density value of the window having the smallest density value.

7. The computer-readable storage medium of claim 6, wherein the window around each pixel location is a square-shaped window that overlaps at least one other window corresponding to a different pixel location.

8. The computer-readable storage medium of claim 6, wherein the first convolution comprises a Gaussian blur, and the first convolution kernel comprises a standard deviation of a Gaussian distribution.

9. The computer-readable storage medium of claim 6, wherein determining whether the input image is a replica of the biometric is further based on applying a density estimation procedure to one or more enrollment images of the biometric.

10. The computer-readable storage medium of claim 6, wherein the biometric comprises a fingerprint of a finger, and the replica comprises a gelatin mold, a graphite mold, or a wood glue mold of the fingerprint of the finger.

11. A device, comprising:
   a biometric sensor; and
   a memory storing instructions; and
   a processor configured to execute the instructions to cause the device to:
      receive, from the biometric sensor, an input image of a biometric;
      generate a first filtered image by applying a first convolution to the input image based on a first convolution kernel;
      generate a second filtered image by applying a second convolution to the input image based on a second convolution kernel;
      compute a gradient residual image by subtracting, for each pixel location of the first and second filtered images, a pixel value in the second filtered image from a corresponding pixel value in the first filtered image;
      apply a density estimation procedure to the gradient residual image to identify areas of varied density; and
      determine whether the input image is a replica of the biometric based on results of the density estimation procedure,
   wherein applying the density estimation procedure comprises:
      for each pixel location of the gradient residual image, summing an amount of gradient present in a window around the pixel location to generate a density value of the window around the pixel location;
      computing an average density value of the density values of the windows;
      determining a count of a number of windows that have a density value that deviates from the average density value by a threshold amount; and
      identifying areas of varied density based on the count.

12. The device of claim 11, wherein the window around each pixel location is a square-shaped window that overlaps at least one other window corresponding to a different pixel location.

13. The device of claim 11, wherein the first convolution comprises a Gaussian blur, and the first convolution kernel comprises a standard deviation of a Gaussian distribution.

14. The device of claim 11, wherein determining whether the input image is a replica of the biometric is further based on applying a density estimation procedure to one or more enrollment images of the biometric.

15. The device of claim 11, wherein the biometric comprises a fingerprint of a finger, and the replica comprises a gelatin mold, a graphite mold, or a wood glue mold of the fingerprint of the finger.

* * * * *